United States Patent [19]

Arnold

[11] Patent Number: 5,965,110
[45] Date of Patent: Oct. 12, 1999

[54] PLAQUE ADSORBENT ORAL COMPOSITION AND METHOD

[76] Inventor: Michael J. Arnold, 791 Newton Way, Costa Mesa, Calif. 92715

[21] Appl. No.: 09/113,911

[22] Filed: Jul. 10, 1998

Related U.S. Application Data

[63] Continuation of application No. 07/609,185, Nov. 2, 1990, Pat. No. 5,804,165.

[51] Int. Cl.⁶ ............................. A61K 9/46; A61K 7/16
[52] U.S. Cl. ................................. 424/44; 424/49; 424/53
[58] Field of Search .................... 424/44, 49–58

[56] References Cited

U.S. PATENT DOCUMENTS

| | | | |
|---|---|---|---|
| 975,354 | 11/1910 | Gruter et al. | 424/49 |
| 975,814 | 11/1910 | Westlake | 424/49 |
| 1,082,681 | 12/1913 | Danner | 424/49 |
| 1,112,180 | 9/1914 | Westenfelter | 424/49 |
| 1,262,888 | 4/1918 | Westlake . | |
| 1,275,275 | 8/1918 | Levinson . | |
| 1,297,494 | 3/1919 | Rhein | 424/49 |
| 1,516,398 | 11/1924 | McDowell | 424/49 |
| 2,035,267 | 3/1936 | Fleischman . | |
| 2,218,172 | 10/1940 | Kokatnur . | |
| 2,275,979 | 3/1942 | Molnar . | |
| 2,820,000 | 1/1958 | Menzies | 424/49 |
| 2,868,655 | 1/1959 | Ladenburg | 99/143 |
| 2,951,791 | 9/1960 | Stearns | 167/82 |
| 3,087,857 | 4/1963 | Davis et al. . | |
| 3,101,299 | 8/1963 | Ferrand | 167/82 |
| 3,227,521 | 1/1966 | Carithers et al. | 424/49 |
| 3,330,732 | 7/1967 | Muhler | 167/93 |
| 3,372,125 | 3/1968 | Hill . | |
| 3,431,339 | 3/1969 | Gyarmathy et al. . | |
| 3,432,338 | 3/1969 | Sickles . | |
| 3,488,288 | 1/1970 | Hill . | |
| 3,518,343 | 6/1970 | Weslh et al. | 424/44 |
| 3,518,344 | 6/1970 | Welsh et al. | 424/44 |
| 3,518,345 | 6/1970 | Welsh et al. | 424/44 |
| 3,574,824 | 4/1971 | Echeandia et al. . | |
| 3,577,490 | 5/1971 | Welsh et al. | 264/120 |
| 3,577,492 | 5/1971 | Welsh et al. | 264/120 |
| 3,577,521 | 5/1971 | Scheller et al. | 424/55 |
| 3,629,468 | 12/1971 | Anderson . | |
| 3,670,076 | 6/1972 | Muhler | 424/157 |
| 3,767,791 | 10/1973 | Gordon et al. | 424/49 |
| 3,772,431 | 11/1973 | Mlkvy et al. . | |
| 3,821,117 | 6/1974 | Breece et al. . | |
| 3,888,976 | 6/1975 | Mlkvy . | |
| 3,903,255 | 9/1975 | Gusmann et al. | 424/44 |
| 3,914,434 | 10/1975 | Bohni | 424/345 |
| 3,935,305 | 1/1976 | Delaney et al. | 424/49 |
| 3,937,321 | 2/1976 | Delaney et al. | 424/84 |
| 3,937,803 | 2/1976 | Delaney et al. | 424/49 |
| 3,937,804 | 2/1976 | Delaney et al. | 424/52 |
| 3,962,417 | 6/1976 | Howell . | |
| 3,976,601 | 8/1976 | Levin . | |
| 4,062,793 | 12/1977 | Schodel . | |
| 4,098,435 | 7/1978 | Weyn | 222/94 |
| 4,127,645 | 11/1978 | Witzel et al. | 424/94 |
| 4,155,868 | 5/1979 | Kaplan et al. . | |
| 4,157,386 | 6/1979 | La Rochelle . | |
| 4,180,467 | 12/1979 | Barth . | |
| 4,181,621 | 1/1980 | Raaf et al. . | |
| 4,267,164 | 5/1981 | Yeh et al. . | |
| 4,302,441 | 11/1981 | Muhlemann et al. . | |
| 4,308,252 | 12/1981 | Tomaich et al. . | |
| 4,367,218 | 1/1983 | Jacobson . | |
| 4,411,885 | 10/1983 | Barels et al. . | |
| 4,414,198 | 11/1983 | Michaelson | 424/44 |
| 4,487,757 | 12/1984 | Kiozpeoplou | 424/44 |
| 4,528,180 | 7/1985 | Schaeffer . | |
| 4,537,778 | 8/1985 | Clipper et al. . | |
| 4,592,487 | 6/1986 | Simon et al. . | |
| 4,592,855 | 6/1986 | Gioffre et al. | 424/49 |
| 4,627,972 | 12/1986 | Gioffre et al. | 424/44 |
| 4,647,451 | 3/1987 | Piechota, Jr. . | |
| 4,753,792 | 6/1988 | Aberg . | |
| 4,818,518 | 4/1989 | Gioffre et al. | 424/44 |
| 4,832,956 | 5/1989 | Gergely et al. | 416/416 |
| 4,923,685 | 5/1990 | Wuelknitz et al. | 424/54 |
| 4,971,782 | 11/1990 | Rudy et al. . | |
| 4,980,154 | 12/1990 | Gordon | 424/53 |
| 4,983,379 | 1/1991 | Schaeffer | 424/52 |
| 5,000,941 | 3/1991 | Chernack | 424/49 |
| 5,008,106 | 4/1991 | Merianos et al. | 424/80 |
| 5,028,414 | 7/1991 | Sampathkumar | 424/53 |
| 5,055,305 | 10/1991 | Young | 416/416 |
| 5,057,305 | 10/1991 | Aberg . | |
| 5,122,365 | 6/1992 | Murayama . | |
| 5,804,165 | 9/1998 | Arnold | 424/44 |

FOREIGN PATENT DOCUMENTS

| | | |
|---|---|---|
| 284579 | 12/1963 | Australia . |
| 20 40 999 | 3/1971 | Germany . |
| 2051499 | 4/1971 | Germany . |
| 1259342 | 2/1969 | United Kingdom . |
| 1269620 | 10/1970 | United Kingdom . |
| WO 88 10110 | 12/1988 | WIPO . |
| WO 92 07550 | 5/1992 | WIPO . |

OTHER PUBLICATIONS

*Cosmetic & Toiletries*, May 1982, "Dentifrices: Pespectives", by Morton Pader, vol. 97, pp. 40–58 J. Soc., Cosmet., Chem., 29, 497–521 (Aug. 1978), "Cosmetic Properties and Structure of Fine Particle Synthetic Precipitated Silicas", by S.K. Wason, pp. 497–521.

*Primary Examiner*—Shep K. Rose
*Attorney, Agent, or Firm*—Lyon & Lyon LLP

[57] ABSTRACT

A non-aqueous liquid plaque adsorbent oral or effervescent dentifrice composition comprising a non-aqueous carbon dioxide source selected from bicarbonate salt, carbonate salt and mixtures thereof, a non-aqueous, water soluble acid source selected from organic acid, partial salt thereof and mixtures thereof, and a carrier adsorbent. Optionally, the composition can include flavoring agent, artificial, non-caloric sweetener, surface active agent, anti-bacterial agent, astringent agent, desensitizing agent, fluoride containing anti-caries agent, gelling agent, chloropyhyllin salt, coloring agent, hydrogen peroxide source and/or excipient. The effervescent dentifrice is preferably employed as one component of a kit also including a debriding product, a hydrogen peroxide product and a bicarbonate dentifrice, the components of the kit being used in combination on a daily basis to synergistically achieve enhanced preventative and remedial oral hygiene.

4 Claims, No Drawings

PLAQUE ADSORBENT ORAL COMPOSITION AND METHOD

This application is a continuation of U.S. Ser. No. 07/609,185 filed on Nov. 2, 1990 now U.S. Pat. No. 5,804,165.

FIELD OF THE INVENTION

The present invention relates to solid and non-aqueous liquid plaque adsorbent oral or effervescent dentifrice compositions, a related combination of compositions in kit form and their method of use. The composition comprises a pharmaceutically acceptable bicarbonate or carbonate salt, a pharmaceutically acceptable organic acid or organic acid salt and a pharmaceutically acceptable carrier adsorbent.

BACKGROUND OF THE INVENTION

Sodium bicarbonate, a bicarbonate salt, is a common household ingredient used in cooking, cleaning, and deodorizing. Sodium bicarbonate alone or in combination with other ingredients, has been recognized and used as a dentifrice since at least the turn of the century and is considered an acceptable and effective alternative dentifrice to the commercially prepared dentifrices. Dentifrice has been a very important tool of preventive dentistry. It is believed that the use of dentifrice in conjunction with a toothbrush has probably accomplished more in the prevention of oral disease than any other oral health procedure. Virtually all oral diseases of bacterial origin could be eliminated by the meticulous application of the self-administrative oral hygiene techniques now available, such as, toothbrush, toothpaste, floss, irrigation devices, and the like. Unfortunately, the average person does not use and has not used these tools effectively. One aim of preventive dentistry has therefore been to improve the efficacy of self-administered oral hygiene procedures to obtain maximum benefit with minimum effort. Various forms of dentifrices have been thought to provide one of the most productive vehicles in the achievement of this aim.

In order to maintain healthy teeth and gums, an individual must constantly battle against tooth pellicle, dental plaque, dental calculus, and food debris. The judicious use of dentifrice in conjunction with the toothbrush is currently used to control these accumulations.

Tooth pellicle is a thin proteinaceous film which forms on the teeth and is not visible to the naked eye. It forms within hours following removal by dental prophylaxis. It is believed that pellicle is formed by the adsorption by teeth enamel of proteins present in saliva. All other oral accumulations form over the pellicle. Dental pellicle and accumulations thereon are considered to be a factor for tooth stains.

Dental plaque is an accumulation that forms over tooth pellicle. After the deposition of the pellicle, microorganisms attach to the pellicle. This is favored by the secretion of bacterial extra-cellular material. After formation, the plaque attacks and provides a suitable site for the accumulation of other substances. The acid generated by the plaque bacteria demineralizes the dental enamel resulting in carious lesions. The bacteria in the plaque are not only the leading cause of caries, they are also the leading cause of periodontal disease, that is, destruction of the gum tissue supporting the teeth. Periodontal disease is a major concern to dental hygiene since it is the major cause of tooth loss, especially in older patients.

When dental plaque mineralizes the accumulates on the tooth surface, it forms dental calculus. Calculus, once formed, is virtually impossible to remove with the toothbrush and available dentifrices. One objective of a dental hygienist is to attempt to remove formed calculus.

Food debris is an important oral accretion which can support the build-up of plaque. The food debris provides nutrients for the plaque bacteria which account for generally all dental problems. The toothbrush, a dentifrice, and floss are ideal for the removal of food debris.

Modern dentifrice comprises a mild abrasive for the removal of stains, a surface active agent or detergent to aid in the cleaning of the teeth and destruction of the plaque bacteria, an anti-caries agent, water, and, optionally, flavoring agents, sweetening agents, viscosity modifiers, desensitizers, and the like. It is still not clear whether an abrasive is needed to remove plaque and pellicle. However, it is recognized that an abrasive is required to remove stain accumulations from teeth. Up until the 1060's, the most common abrasives used in dentifrices were dicalcium phosphate dihydrate, calcium carbonate, and insoluble sodium metaphosphate. However, these abrasives since the 1960's have been gradually replaced by aluminum oxide trihydrate and forms of hydrated silica. Over half the dentifrices presently used employ hydrated silica abrasives because of their superior flavor release properties and excellent compatibility with fluoride salts. Most of the silica used is of the amorphous form since the crystalline silica structure is considered too hard to use safely with gum tissue. In addition, amorphous silicas tend to break down and shear under pressure because of their porosity and friability and, thus, are not excessively abrasive to teeth enamel or dentine. The dentifrices compounded with conventional abrasives contain about 40 to 50 percent by weight of abrasive. Dentifrices compounded with amorphous silica abrasives have a much lower abrasive loading (from about 10 to about 20 percent by weight).

The fluoride dentifrices, the anti-caries dentifrices, are normally compounded with sodium fluoride, sodium monofluorophosphate or stannous fluoride as a fluoride source. The concentration of fluoride salt is normally about 100 ppm. The function of fluoride in combating tooth decay is not fully understood nor is the mode of action fully understood. Some dental experts contend that the fluoride ion in the dentifrice interacts with tooth enamel to form a fluorophosphate structure, such as fluoratatite, which is more resistant to attack by the acids generated by dental plaque bacteria. Other experts contend that the dental enamel attached by an acid can be remineralized and that the fluoride enhances the rate of that remineralization and makes the resulting crystalline structure more resistant to further attack by acid. A third hypothesis is that the fluoride ion inhibits metabolic processes in plaque bacteria reducing their ability to produce acid. Possibly the role of fluoride in combating tooth decay combines all three of these actions.

Almost all dentifrices contain a surfactant primarily to enhance foaming action of the dentifrice. Almost all dentifrices either employ sodium lauryl sulfate or sodium dodecyl benzene sulfate as dentifrice surfactants.

In most dentifrices, the flavoring agent has no hygienic purpose. The flavoring is added to the dentifrice to make it more acceptable to the consuming public, to mask the flat taste of the other ingredients and to freshen the breath. The most common flavoring agents are mint, anise-type flavors, and cinnamon. Peppermint flavoring is slowly being phased out.

A variety of thickening agents are used in dentifrices to give the dentifrice proper body or structure. Silicas have been used extensively, especially in clear gel dentifrices, to give structure. In the opaque dentifrices, a number of organic gums are used, such as, xantham gum, carbosymethyl cellulose, acrylic acid polymers, polyacrylic acid resins, and the like. A number of dentifrices also contain desensitizing agents for patients with hypersensitive teeth. The most common desensitizers are strontium chloride and potassium nitrate. It is noteworthy that sodium citrate is also recognized as a desensitizing agent.

For ideal oral hygiene, the teeth would be brushed with a dentifrice, flossed, and irrigated following each meal and snack. Unfortunately, the time restraints in the lives of most people and the lack of convenient facilities do not allow this luxury. This is unfortunate, especially since the average life span of a typical person has increased substantially over the last 50 years. Children and young adults are the most susceptible to caries. Adults rarely get caries because of the chemical and physiological change of their saliva. However, adults are more prone to periodontal disease which is the leading cause of tooth loss. Adults are more susceptible to periodontal disease with increasing age. Plaque build-up is recognized as the principal contributor to such disease. Thus, it is very desirable to develop means for removing plaque from the teeth promptly after its formation.

It is an object of the present invention to provide a dry oral wash composition that can be inserted into the oral cavity following a meal or snack to rinse or wash the mouth free of organic debris and inhibit the formation of plaque.

It is a further object of the present invention to provide an oral non-aqueous dentifrice composition that can be taken to clean the oral cavity of organic debris and remove plaque from the teeth.

An additional object is to provide a composition that will neutralize the acids in the oral cavity.

Another object of the present invention is to provide an anti-plaque composition that will inhibit the build-up of plaque on the teeth and inhibit the population growth of plaque bacteria in the oral cavity.

Others in the field of oral hygiene have attempted to make such compositions. For example, U.S. Pat. No. 1,297,494 is directed to an effervescent, solid dentifrice comprising an acid salt and a bicarbonate salt which are mutually reactive in the presence of moisture to produce $CO_2$ and an initially weak acid solution to contact the surface of the teeth. The solution acted primarily to dislodge plaque adhesions from enamel surface and the $CO_2$ and the irrigation of the acid solution away from the enamel surface. The period of acid activity is limited as to preclude enamel decalcification and aids in the reactivation of the alkaline addition of the saliva in the mouth. The composition can be optionally compounded with abrasives such as calcium carbonate (chalk), surface active agent such as the soap of sodium oleate, a sweetening agent such as saccharine and flavoring agents such as oil of peppermint. The dentifrice could be employed as a dry powder or a paste compounded with thickening agent such as glycerine or gum arabic free of water. The dentifrice is to be used in conjunction with a toothbrush.

SUMMARY OF THE INVENTION

The present invention is directed to a non-aqueous effervescent oral composition comprising by weight percent 15 to 90 percent of a non-aqueous, water soluble, pharmaceutically acceptable carbon dioxide source selected from the group consisting of bicarbonate salt, carbonate salt and mixtures thereof, 5 to 20 percent by weight of a non-aqueous, water soluble, pharmaceutically acceptable acid source selected from the group consisting or organic acid, partial salt of an acid and mixtures thereof, and from about 10 to about 25 percent by weight of a non-aqueous, pharmaceutically acceptable carrier adsorbent. Optionally, the composition can include 0.1 to about 2 percent by weight of a non-aqueous flavoring agent, from about 0.1 to about 5 percent of a non-aqueous, non-caloric sweetening agent, from about 1 to about 10 percent by weight of non-aqueous excipients, from about 0.1 to about 3 percent by weight of a non-aqueous surfactant, from about 0.1 to about 5 percent of non-aqueous pharmaceutically acceptable anti-bacterial agent, from about 0.1 to about 3 percent of a non-aqueous, pharmaceutically acceptable desensitizing agent, from about 0.1 to about 2 percent of a non-aqueous, pharmaceutically acceptable chloropyhyllin salt, from about 1 to about 35 percent of a non-aqueous, pharmaceutically acceptable hydrogen peroxide source and up to 10 percent by weight of other agents beneficial to the therapeutic effect, stability, homogeneity, and patient acceptability of the composition.

Sufficient bicarbonate or carbonate salt is employed in the composition so that in an aqueous mixture of the composition, the acid or acid salt is completely neutralized by the bicarbonate or carbonate salt. Thus, a stoichiometric excess of bicarbonate or carbonate salt with respect to the acid is utilized in the composition.

The composition can be administered as a tablet, as a powder, as a capsule which is soluble in saliva, or as an anhydrous solid liquid mixture employing a non-aqueous, water miscible, pharmaceutically acceptable vehicle, such as glycerine, propylene glycol, or pharmaceutically acceptable water miscible oil, as the liquid carrier or vehicle.

The plaque removal and anti-plaque properties of the composition are not fully understood. It is believed that when the composition is placed in the oral cavity, the saliva wets the composition dissolving the bicarbonate or carbonate salt and the acid or acid salt. The solubilized bicarbonate or carbonate ion and the acid components in the resulting saliva mixture undergo a rapid acid-base reaction generating carbon dioxide gas. The resulting effervescent action sweeps the saliva mixture through the oral cavity, between the teeth, into crevices and cavities in the teeth, and into the juncture of the gums and teeth. It is believed that the bicarbonate or carbonate ion, the acid, acid salt components, and the acid bicarbonate and carbonate salt reaction product have a solubilizing effect on plaque components that loosens the plaque and other organic debris from the surface of the teeth. The effervescent action of the saliva sweeps the loosened plague and organic debris from the surface of the teeth. Plaque particles swept from the teeth and other organic debris are adsorbed on the carrier adsorbent and are thus effectively removed as an organic source for further plaque formation. The excess soluble acid in the saliva stimulates the salivary glands to excrete additional saliva. This additional saliva further dissolves the soluble components of the composition to generate further solubilize bicarbonate or carbonate ion and acid which react to form additional $CO_2$. When the acid has fully reacted with the bicarbonate or carbonate ion, the effervescent ceases and the pH of the saliva in the oral cavity stabilizes at a value between about 7 and 12 due to the buffering action of the excess bicarbonate and/or carbonate ion.

The saliva solution can be swished through the mouth to clean surfaces of the teeth, especially the surfaces between adjoining teeth, and sweep out loose organic debris and biomass. Preferably the saliva solution is allowed to remain in the oral cavity for at least one minute, preferably at least 3 to 6 minutes, to enhance the cleaning activity of the solution. The resulting saliva mixture can then either be swallowed or expectorated. It is noteworthy that the carrier adsorbent particles remaining after expectoration significantly safeguards the teeth and gums from bacterial colonization. Plaque bacteria and food debris are given residence on the surfaces of the carrier adsorbent which eventually gets flushed away thereby reducing the level of plaque.

All the ingredients of the effervescent dentifrice are non-aqueous, pharmaceutically acceptable materials currently utilized in toothpastes, toothpowders, and oral rinses.

The invention is also directed a combination of dentifrice compositions, preferably in kit form, and contemplated for use in combination with each other for achieving enhanced preventative and remedial oral hygiene including control of gum disease, dissolution of plaque and/or prevention of plaque accumulation. The four components of the kit include (1) a debriding solution having as an essential solution sodium bicarbonate (5–10% by weight) in aqueous solution, preferably with flavoring, (2) the plaque oral composition or effervescent dentifrice tablet described elsewhere herein, (3) a product preferably in the form of a viscous and dilute aqueous solution, containing hydrogen peroxide (1.5–6% by weight) or an equivalent hydrogen peroxide precursor, and (4) a dentifrice containing as an essential component a sodium and/or potassium bicarbonate salt (10–65% by weight).

The invention also contemplates a method of combined use for the kit of four components as set forth above for the purpose of acting in combination for enhanced preventative and remedial oral hygiene.

The method of combined use for the four components of the kit referred to above include use of the debriding solution in the oral cavity before normal tooth brushing and preferably prior to use of the hydrogen peroxide solution or jelly and the bicarbonate dentrifrice. The effervescent dentifrice or plaque adsorbent oral composition, preferably in tablet form, is used 1–10 times daily, preferably at least about 3–5 times daily, for example after meals or snacks or whenever freshening of the oral cavity is desired. The hydrogen peroxide, preferably in a jelly form, and the bicarbonate dentifrice are used in combination by direct application to a toothbrush, for example, from separate containers to form a-jelly-paste that is slightly effervescent when applied to the teeth and gums.

DETAILED DESCRIPTION OF THE INVENTION

The effervescent composition of the present invention comprises a non-aqueous, water soluble, pharmaceutically acceptable carbon dioxide source selected from the group consisting of bicarbonate salt, carbonate salt, and mixtures thereof; a non-aqueous, water soluble pharmaceutically acceptable acid source selected from the group consisting of organic acids, partial salt thereof and mixtures thereof; and a non-aqueous, pharmaceutically acceptable carrier adsorbent.

A non-aqueous, water soluble, pharmaceutically acceptable bicarbonate or carbonate salt, such as lithium bicarbonate, lithium carbonate, sodium bicarbonate, sodium carbonate, potassium bicarbonate, potassium carbonate, calcium carbonate, magnesium carbonate, ammonium bicarbonate, ammonium carbonate, or the like, may be employed in the composition. Mixtures of such salts may also be utilized. At least a twofold stoichiometric excess of the bicarbonate or carbonate salt with respect to the organic acid will be employed in the composition. Preferably, at least one water soluble bicarbonate or carbonate salt will be employed in the composition, the balance being made up of water soluble or partially water soluble bicarbonate or carbonate salt. Water soluble bicarbonates and carbonate salts are those salts which have a solubility of at least 100 grams of salt per liter of water at 100° C. The partially soluble bicarbonate and carbonate salts are those salts that have a solubility of less than 100 grams of salt per liter of water at 100° C.

The composition comprises by weight percent 15 to 90% of bicarbonate and/or carbonate salt, preferably from 45 to about 85%, and most preferably from about 55 to 75%.

A non-aqueous, water soluble, pharmaceutically acceptable organic acid or partial salt of an organic acid can be employed in the present composition. Examples of such organic acids include, but are not limited to, maleic acid, citric acid, adipic acid, ascorbic acid, malic acid, tartaric acid, succinic acid, pyruvic acid, oxaloacetic acid, alpha-ketoglutaric, fumaric acid, isocitric acid, cis-aconitic acid, lactic acid, alginic acid, amino acids, and the like. Partial salts of such organic acids that may be employed in the present invention, include the lithium, sodium, potassium, calcium, and magnesium slats of maleic acid, citric acid, adipic acid, malic acid, ascorbic acid, succinic acid, fumaric acid, and the like. the preferred acids are the acids found in natural fruits, such as citric acid, maleic acid, and malic acid. Especially preferred are citric acid and tartaric acid because of their pleasant taste to the human palate.

The effervescent composition comprises from about 5 to about 20 percent by weight of the organic acid or partial salt thereof. Preferably from about 7.5 to about 12.5 weight percent, and most preferably from about 8 to about 12 weight percent.

The pharmaceutically acceptable carrier adsorbents are solid inorganic adsorbents that have a very limited solubility in aqueous solutions. The adsorbents have a small particle size, large surface area, and good adsorption properties for anions and biomass. The adsorbents used in the present composition are selected from silicon, alumina, aluminosilicate, sodium aluminum silicate, zirconium silicates, and the like.

Natural silicas and synthetic silicas may be employed in the present invention. Synthetic silicas include synthetic fumed silicas, synthetic silic gels and synthetic precipitated silicas which are prepared by vapor phase processes or by liquid phase processes. Precipitated silicas and silica gels are often termed hydrated silica and fumed silicas are often termed silicas. Fumed silicas are prepared by the hydrolysis of silicon tetrachloride vapor in a flame of hydrogen and oxygen at elevated temperatures. Silica gels and precipitated silicas are prepared by the acidulation of aqueous sodium silicate solutions with an acidification agent, such as sulfuric acid. To produce silica gels, the reaction is generally conducted under acid conditions and to produce precipitated silicas the reaction is carried out under alkaline condition. IN the manufacture of silica gels, a hydrosol is first produced, and then a hydrogel is formed. When the hydrogel is washed and dried from an organic medium without shrinkage of the structure, the end product is called an aerogel. All other silica gel products are called xerogels. Fumed silicas in many respects are similar to silica gels and precipitated silicas. Under electron microscope, differences in the structure of fumed silica, silica gel, and precipitated silicas can be observed. However, the major differences and similarities between these types of silicas are shown in the following table.

TABLE I

Comparative Properties of three Types of Silicas

| PROPERTY | FUMED | SILICA GEL | PRECIPITATED |
|---|---|---|---|
| Surface Area (m$^2$/g) | 200–400 | 300–1000 | 60–300 |
| Type Surface Area | External | Internal | External |
| Porosity | Non-porous | Porous | Both |
| Bulk Density, g/l | 32–64 | 96–160 | 160–192 |
| 5% pH | 3–4.2 | 4–7.5 | 6.5–7.5 |
| Silanol Groups/nm$^2$ | 2–4 | 4–8 | 8–10 |
| Ave. Particle Diameter (nm) | 14 | — | 18 |
| % SiO$^2$ (lighted Basis) | 99.8 (Min) | 99.5 | 98.0 |

Further information regarding silicas can be found in the paper by S. K. Wason published in the Journal of the Society of Cosmetic Chemists 29, 497–521 (August 1978) which is incorporated herein by reference.

The alumina adsorbents may be of the hydrated or unhydrated type. The commonly used alumina polishing agent is in the form of flat flakes or alpha-alumina crystals of disk- or plate-like configurations. The flakes have a mean particle diameter of less than about microns, e.g., about 2 to 7 microns. The flat alpha-alumina crystals and a process for their preparation is described in U.S. Pat. No. 3,121,623.

The preferred carrier adsorbents are synthetic precipitated silica. Especially preferred are synthetic precipitated amorphous silica. Synthetic precipitated silicas have an average particle size of from about 1 to about 10 microns, an oil absorption of from about 250 to about 75 cc per 100 grams (determined by Linseed Oil Rub-Out Method), a surface area of from about 100 to about 300 square meters per gram (measured by the BET Method) and a sodium sulfate content of less than 5% by weight (determined by the conductivity method). The especially preferred synthetic precipitated amorphous silicas having low structure, an average particle size of about 9 microns, an oil absorption of about 90 cc per 100 grams, a sodium sulfate content of about 1% by weight, and a surface area of about 250 square meters per gram. ZEO-49 and ZEODENT-113 brand synthetic precipitated amorphous silicas supplied by J. M. Huber Corporation of Havre de Grace, Md., have been employed in the present composition with good results.

The present composition comprises about 1 to about 35 percent of the carrier adsorbent, preferably from about 10 to about 30 percent and most preferably from about 15 to about 25 percent.

The carrier adsorbent adsorbs plaque particles, organic debris and biomass loosened or washed off the teeth and from the surfaces of the oral cavity. The organic material is adsorbed on the carrier adsorbent and, thus, is no longer available for plaque formation.

It appears that bicarbonate and carbonate ion is also adsorbed on the carrier adsorbent. As the bicarbonate and carbonate ion is consumed in the saliva mixture, bicarbonate and carbonate ion in released from the carrier, adsorbent. The carrier adsorbent remaining in the oral cavity provides a source of bicarbonate and carbonate ion. When a composition is compounded without the carrier adsorbent, the bicarbonate and carbonate ion concentration quickly drops within the oral cavity, possibly because of enzymatic activity and/or irrigation of the mouth by saliva. However, in the present composition, there is a storage source of bicarbonate and carbonate ion. Thus, the present composition has the property of enhancing the longevity of the beneficial properties of bicarbonate and carbonate ion in the oral cavity. Bicarbonate and carbonate ion exhibit bactericidal properties and are effective cleansers, deodorizers, and acid neutralizers. Thus the bicarbonate and carbonate ion neutralizes the acids in the oral cavity, gives the oral cavity a clean, fresh feel, and deodorizes the breath.

The composition can be compounded as a tablet, as a powder, as a capsule, and/or as a non-aqueous mixture. When the composition is compounded as a tablet, the tablet will contain the normal tablet forming agents such as sorbitol, mannitol, and zinc stearate to bind the tablet and lubricate the tablet. The tablet may also contain desiccants, such as anhydrous silica gel, anhydrous sodium sulfate, anhydrous sodium, calcium or magnesium carbonate, and the like to maintain the anhydrous condition of the tablet and prevent reaction between the bicarbonate and carbonate salt and the acid. Similarly, the powder may contain a desiccant to maintain the powder in an anhydrous state to prevent reaction between the sale and the acid. Similarly, the powder may contain a desiccant to maintain the powder in an anhydrous state to prevent reaction between the salt and the acid. When a composition is delivered to the oral cavity in the form of a capsule, the composition is normally in a powdered form which may optionally contain the desiccant to keep the powder dry. The capsule will be prepared from the conventional water soluble capsule material, such as, gelatin or the like, so that the capsule dissolves in the mount by the action of saliva.

The composition may also be prepared in the form of a non-aqueous liquid mixture employing a non-aqueous, water miscible, pharmaceutically acceptable liquid carrier, such as glycerol, polyethylene glycol, or any suitable mixture thereof. The liquid mixture is compounded in the anhydrous state to prevent any reaction between the salt and the acid. Non-aqueous dispersants and viscosity modifiers which are pharmaceutically acceptable may be added to the non-aqueous vehicle to suspend the insoluble constituents of the composition in the vehicle and to increase or decrease the viscosity of the mixture.

The typical dosage of the present composition is from about 500 to about 2000 milligrams, excluding the non-aqeuous liquid vehicle, preferably about 750 milligrams. The composition may be formed into tablets or capsules representing a single dosage unit or partial dosage unit. For example, the composition can be formed into tablets each weighing 250 milligrams or 375 milligrams or formed into capsules weighing 500 milligrams excluding the weight of the capsule. When a composition is compounded into a non-aqueous liquid mixture, the mixture will contain a unit weight per unit volume of the mixture. For example, the mixture can be compounded to contain 250 milligrams of the composition per tablespoon of the liquid mixture. No untoward effects have been observed with the use of the composition of the present invention. If the sodium loading of the dentifrice composition is of concern to a patient, the composition can be formulated with non-sodium salts, such as potassium salts, calcium salts, magnesium salts, and the like.

The effervescent composition may also contain non-caloric sweetening agents, flavoring agents, surfactants, and thickeners to enhance acceptability of the composition to the human palate. Preferably, the composition is sweetened with non-sugar based sweeteners such as sodium saccharin, calcium cyclamate, and aspartame (N-L-alpha-aspartyl-L-phenylalanine methyl ester). The amount of non-sugar sweetener employed in the present composition is not critical. Normally, the amount of non-sugar sweetener used in the composition will be from about 0.1 to about 5 percent by weight of the total composition, preferably from about 0.1 to about 0.5 weight percent.

The effervescent dentifrice composition can also be flavored with non-aqueous liquid flavoring agents and solid flavoring agents, such as menthol, powdered wintergreen, peppermint oil, oil of cloves, extract of vanilla, cinnamon powder, spearmint flavoring, mint flavoring, orange flavoring extract, lemon flavoring extract, cherry flavoring, chocolate flavoring, and the like. The amount of flavoring agent employed in the present composition is not critical. The amount of flavoring agents will normally be from about 0.1 to about 3 percent by weight of the total composition, preferably between about 0.1 and 2 weight percent, and most preferably between about 0.1 and 1.5 weight percent.

Optionally, the effervescent composition may be compounded with a non-aqueous, water miscible, pharmaceutically acceptable surface water soluble active agent to enhance the wetting of the composition by saliva, to optimize the reaction between the bicarbonate and carbonate salt in the acid and to enhance the foaming action of the saliva mixture after delivery of the composition in the oral cavity. The amount of surface active agent compounded in the composition is from about 0.1 to about 3 weight percent of the total composition, preferably from about 0.1 to about 2 weight percent. The surface active agents also have antibacterial activity which will lower the microbial population in the oral cavity after use of the present composition. Surface active agent will also enhance the power of the composition to dislodge biomass (plaque and other organic debris) from the surface of the teeth. A surface active agent is preferably used in the composition to aid in the prophylactic action and in dispersion of the composition throughout the oral cavity. A non-aqueous, pharmaceutically acceptable surfactant that may be use din the present composition includes the higher alkyl sulfates, such as sodium lauryl sulfate or other suitable alkyl sulfate having 8 to 18 carbon atoms, water soluble salts of sulfonated monoglycerides of higher fatty acids, such as sodium coconut monoglyceride sulfonate, or other suitable monoglyceride of a fatty acid having 10 to 18 carbon atoms, slats of higher fatty acid amides or lower aliphatic amino acids, such as taurine or sarcosine, or other amino acids from 2 to 6 carbon atoms, such as sodium N-methyl-N-palmityl taurinate, sodium N-lauryl or sarcosinat, sodium N-mysistyl sarcosinate, sodium N-palmitoyl sarcosinate and the like. Water soluble salts of the esters of fatty acids with glycerol monosulfate, such as the sodium salt of monosulfated monoglycerides of hydrogenated coconut oil fatty acids, water soluble salts of olefin sulfonates, such as alkene sulfonates or hydroxyalkenes or mixtures thereof having 12 to 16 carbon atoms, and water soluble soaps of higher fatty acids having 12 to 18 carbon atoms, such as coconut fatty acids may also be used in the present composition. Mixtures of surfactants may be used if desired. The preferred surfactant is sodium lauryl sulfate.

Non-aqueous, pharmaceutically acceptable antibacterial compounds may also be compounded in the composition. Such compounds include cationic surface active agents, such as di-isobutylphenoxyethoxyethyl demethyl benzyl ammonium chloride, cetyl pyridinium chloride, benzyl dimethyl stearyl ammonium chloride, tertiary amines having one fatty alkyl group of from 12 to 18 carbon atoms and 2 polyoxyethylene groups attached to the nitrogen and the like. The amount of anti-bacterial composition will be from about 0.01 to about 5 weight percent, preferably between about 0.25 and about 2 weight percent.

The composition may also be compounded with non-aqueous, pharmaceutically acceptable astringent agents, such as aluminum sulfate, and/or with non-aqueous, pharmaceutically acceptable desensitizing agents for persons with sensitized teeth. Desensitizing agents may be employed in the composition include strontium chloride, potassium nitrate, zinc chloride, and monosodium citrate. the amount of astringent agent and/or desensitizing agents will normally be from about 0.1 to about 15 percent by weight, preferably from about 0.1 to about 3 percent.

Optionally, the composition may be compounded with a solid, non-aqueous, water miscible, pharmaceutically acceptable jelling agent to increase the viscosity of the saliva mixture formed when the composition is administered in the oral cavity. The thickened saliva mixture will inhibit the escape of carbon dioxide gas to maintain a high bicarbonate ion concentration and to inhibit the escape of hydrogen peroxide, if a hydrogen peroxide source is present in the saliva mixture.

Suitable jelling agents include gums and thickening agents such as carboxymethyl cellulose, gum tragacanth, gum arabic, gum Karays, sodium alginate, hydroxyethyl cellulose, methyl and ethyl cellulose, carrageenan, xanthan gum, polyvinyl pyrrollidone, silica aerogels and the like.

The amount of jelling agent compounded in the composition is from about 0.1 to about 30% by weight, preferably from about 0.5 to about 20%.

The composition may also be compounded with non-aqueous, pharmaceutically acceptable fluoride containing anti-caries agents, such as stannous fluoride, sodium fluoride, and sodium monofluorophosphate. sufficient fluoride anti-caries agent is added to the composition to give a fluoride concentration of about 100 to about 5000 ppm (parts per million) in the effervescent dentifrice composition, preferably from about 100 to about 1000 ppm. It appears that a concentration of 0.05 percent by weight sodium fluoride is an effective anti-caries concentration.

The composition may also be formulated with a non-aqueous, pharmaceutically acceptable hydrogen peroxide source, such as sodium or potassium perborate, disodium or dipotassium peroxy dicarbonate, sodium or potassium carbonate sequi (peroxy hydrate) and the like. These compounds when wetted with water or saliva form hydrogen peroxide. Hydrogen peroxide is an effective bactericide. Accordingly, the inclusion of a hydrogen peroxide source in the composition enhances the anti-plaque properties of the composition. It also appears that hydrogen peroxide hardens the gum tissue and promotes the healing of gum tissue, thus combating periodontal disease. The composition is optionally compounded with about 1 to about 35% by weight of a hydrogen peroxide source, preferably with between about 1 and 15%, and most preferably with between about 1 and 10%.

The composition can also include non-aqueous, pharmaceutically acceptable tableting aids, such as excipients and lubricants, to aid in forming the composition into pills or tablets. Tableting aids that can be employed in the present invention include stearic acid, magnesium stearate, dextrose, sorbitol, high molecular weight polyethylene glycol (MW of 6000–7500), siloxane polymer, acacia powder, mannitol, and the like. The amount of tableting aids included in the composition is not critical, and those skilled in pill and tablet formulations will employ the appropriate amounts to prepare tablets and pills of appropriate strength, wetability, and disintegration properties for the practice of this invention.

The ZEO-49 and ZEOSYL-200 silica carrier adsorbents used in the following examples are synthetic precipitated amorphous silicas supplied by the J. M. Huber Corporation of Havre de Grace, Md. ZEO-49 silica has an average particle size of 9 microns, an oil adsorption of 92 cc per 100 grams (Linseed Oil Rub-Out Method), a surface area of 250 $M^2/g$ (BET Method), sodium sulfate concentration of 1% by weight, and a low structure. ZEOSYL-200 silica has an average particle size of 5 microns, an oil adsorption of 200 cc per 100 grams, a surface area of 250 $m^2/g$, a sodium sulfate concentration of 1.5% by weight, and a high structure.

The following examples further illustrate practice of the present invention. All ingredients employed in the effervescent composition are dry and moisture-free. The ingredients are compounded and stored in a moisture-free environment to prevent reaction of the ingredients.

EXAMPLE 1

The following ingredients are supplied as fine powders, all of which pass through a 320 mesh screen. The components are added together and then thoroughly mixed to form a homogeneous mixture. The final composition is sealed into jars, and no deterioration or reaction between the bicarbonate and the acid was noted over a period of twelve days. A capful of the composition is taken into the oral cavity following each meal and snack. After the material effervesces, the material is swished through the mouth for between 3 to 6 minutes. The material is then expelled or swallowed. Following the effervescent reaction, the surface of the mouth and tongue and the teeth feel clean, substantially identical to the feeling experienced after brushing. This procedure was followed for 10 days without observation of any significant plaque build-up. during the 10 day period, the teeth were not brushed or flossed.

| COMPONENT | AMOUNT |
|---|---|
| sodium bicarbonate | 14.23 grams |
| J. M. Huber Corporation brand ZEO-49 silica | 4.22 grams |
| citric acid | 2.25 grams |
| menthol | 0.21 grams |
| NUTRASWEET brand artificial sweetener | 0.81 grams |
| powdered wintergreen | 0.35 grams |
| sodium dodecyl sulfate | 0.16 grams |
| stannous fluoride | 0.10 grams |
| TOTAL | 22.01 grams |

After use of the above formulation, the teeth may be brushed to remove biomass debris remaining on the teeth and flossed to enhance the removal of plaque.

EXAMPLE 2

The following effervescent dentifrice composition is prepared with the following ingredients supplied in powdered form. All ingredients pass through a 320 mesh screen. The components are added together and thoroughly mixed to form a homogenous powder. After thorough mixing, the powdered composition is stored in sealed containers.

| Component | Amount |
|---|---|
| sodium bicarbonate | 10.42 grams |
| citric acid | 1.55 grams |
| J. M. Huber Corporation brand ZEO-49 silica | 3.53 grams |
| NUTRASWEET brand artificial sweetener | 0.61 grams |
| powdered wintergreen flavoring | 0.26 grams |
| menthol | 0.11 grams |

| Component | Amount |
|---|---|
| sodium dodecyl sulfate | 0.08 grams |
| TOTAL | 16.56 grams |

The above composition was utilized in the same manner as the composition of Example 1. Optionally, the above composition can be further compounded with 1.0 grams of sorbitol and 0.25 grams of zinc stearate and formed into tablets, each tablet weighing 750 mg. The tablets are sealed in bottles or in impervious metal foil packages to prevent absorption of water and reaction between the bicarbonate and acid.

To reduce sodium loading of the composition, the above formulation can be compounded with the 5 grams of sodium bicarbonate and 6 grams of potassium bicarbonate in place of 10.42 grams of sodium bicarbonate.

EXAMPLE 3

A more active anti-bacterial composition is prepared by adding 0.20 grams of cetyl pyridinium chloride to the composition of Example 2.

EXAMPLE 4

A desensitizing effervescent composition is prepared by adding 0.21 grams of strontium chloride to the composition of Examples 1, 2 or 3.

EXAMPLE 5

An alternative desensitizing-astringent composition is prepared by addition 0.12 grams of strontium chloride and 0.1 grams of zinc chloride to the compositions of Examples 1, 2 or 3.

EXAMPLE 6

A desensitizing composition is prepared by adding 0.21 grams of strontium chloride to the composition of Example 2.

EXAMPLE 7

A low sodium effervescent composition is prepared from the following components in the amounts specified. The components are all reduced to fine powders; all of which pass through a 320 mesh screen. The components are added together and then thoroughly mixed to form a homogenous mixture. The composition is utilized in the same manner as the compositions of Examples 1 and 2.

| Component | Amount |
|---|---|
| calcium carbonate | 5.0 grams |
| magnesium carbonate | 5.0 grams |
| potassium bicarbonate | 1.0 grams |
| citric acid | 2.5 grams |
| sodium saccharin | 0.3 grams |
| powdered wintergreen | 0.2 grams |
| J. M. Huber Corporation brand ZEO-49 silica | 4.0 grams |

EXAMPLE 8

A more flavored composition compared to the composition of Example 7 is prepared from the following components in the amounts indicated:

| Component | Amount |
| --- | --- |
| calcium carbonate | 5.0 grams |
| magnesium carbonate | 1.0 grams |
| sodium bicarbonate | 1.0 grams |
| citric acid | 2.5 grams |
| sodium saccharin | 0.3 grams |
| powdered wintergreen | 0.2 grams |
| menthol | 0.11 grams |
| J. M. Huber Corporation brand ZEO-49 silica | 2.5 grams |

EXAMPLE 9

An effervescent composition suitable for delivery in non-aqueous liquid vehicle is prepared from the following ingredients in the amounts indicated. All the ingredients are obtained in a fine powdered form; all passing through a 320 mesh screen. The dry solid ingredients are mixed together to form a homogenous mass. The powder is then dispersed in the non-aqueous liquid vehicle to obtain a non-aqueous liquid mixture. The mixture is thoroughly shaken before a dosage is taken into the oral cavity to insure the proper dosage unit.

| Component | Amount |
| --- | --- |
| sodium bicarbonate | 15.0 grams |
| J. M. Huber Corporation brand ZEO 49 silica | 4.1 grams |
| ascorbic acid | 1.0 grams |
| citric acid | 2.0 grams |
| menthol | 0.15 grams |
| NUTRASWEET brand artificial sweetener | 0.90 grams |
| powdered wintergreen | 0.4 grams |
| sodium dodecyl sulfate | 0.18 grams |
| glycerine | 4 fld. oz. |
| propylene glycol | 28 fld. oz. |

The above formulation provides a liquid mixture that will give a dosage of about 750 milligrams of the effervescent composition per fluid ounce of the liquid mixture.

EXAMPLE 10

The following effervescent dentifrice composition is prepared from the following ingredients in the specified amounts. All ingredients are supplied in powdered form and pass through a 320 mesh screen. The components are added together and thoroughly mixed to form a homogenous powder. After thorough mixing, the powdered composition is stored in sealed containers.

| Component | Amount |
| --- | --- |
| calcium bicarbonate | 11.5 grams |
| citric acid | 2.0 grams |
| J. M. Huber Corporation brand ZEO-49 silica | 3.5 grams |
| sodium saccharin | 0.40 grams |
| menthol | 0.10 grams |
| sodium dodecyl sulfate | 0.16 grams |
| powdered wintergreen | 0.32 grams |
| KELTOSE brand thickener (a product of Merck & Co., Inc.) | 3.0 grams |
| TOTAL | 21.08 grams |

The KELTOSE brand thickener thickens the composition when it is taken in the oral cavity to form a thick effervescent pasty composition.

EXAMPLE 11

The following effervescent dentifrice composition is prepared with the following ingredients in the amounts specified. All ingredients are supplied in powdered form and pass through a 320 mesh screen. The components are added together mixed to form a homogenous powder. After thorough mixing, the composition is stored in sealed containers.

| Component | Amount |
| --- | --- |
| sodium bicarbonate | 10.42 grams |
| citric acid | 1.55 grams |
| J. M. Huber Corporation brand ZEO-49 silica | 3.55 grams |
| sodium saccharin | 0.40 grams |
| menthol | 0.11 grams |
| sodium perborate | 0.20 grams |
| wintergreen flavoring | 0.30 grams |
| sodium dodecyl sulfate | 0.13 grams |
| TOTAL | 16.66 grams |

The above composition when inserted into the oral cavity and wetted with saliva forms an effervescent mixture containing carbon dioxide gas and hydrogen peroxide gas. The hydrogen peroxide is an efficient bactericidal component and lowers the bacterial population of the oral cavity.

EXAMPLE 12

The following effervescent dentifrice composition is prepared with the following ingredients in the amounts specified. All ingredients are supplied in powdered form and pass through a 320 mesh screen. The components are added together and thoroughly mixed to form a homogenous powder. After thorough mixing, the powdered composition is stored in sealed containers.

| Component | Amount |
| --- | --- |
| sodium bicarbonate | 11.75 grams |
| citric acid | 1.80 grams |
| J. M. Huber Corporation brand ZEOSYL 200 silica | 2.00 grams |
| J. M. Huber Corporation brand ZEO-49 silica | 2.30 grams |
| sodium dodecyl sulfate | 0.09 grams |
| menthol | 0.10 grams |
| sodium saccharin | 0.45 grams |
| wintergreen flavoring | 0.32 grams |
| TOTAL | 18.81 grams |

The above composition contains carrier adsorbents of high structure and low structure.

EXAMPLE 13

The composition of Example 12 can be formulated to be more palatable to children by adding more flavoring agent and sweeteners. Such a composition contains 0.61 grams of sodium saccharin rather than 0.45 grams and 0.11 grams of powdered spearmint flavoring in addition to the 0.32 grams of-powdered wintergreen flavoring.

EXAMPLE 14

The following effervescent dentifrice composition is prepared with the following ingredients supplied in powdered form in the amounts specified. All ingredients pass through a 320 mesh screen. The components are added together and thoroughly mixed to form a homogenous powder. After thorough mixing, the powdered composition is stored in sealed containers.

| Component | Amount |
| --- | --- |
| sodium bicarbonate | 10.42 grams |
| J. M. Huber Corporation brand ZEO-49 silica | 3.60 grams |
| citric acid | 1.60 grams |
| sodium dodecyl sulfate | 0.12 grams |
| sodium saccharin | 0.31 grams |
| powdered wintergreen flavoring | 0.30 grams |
| menthol | 0.11 grams |
| titanium dioxide | 0.05 grams |
| TOTAL | 16.61 grams |

The above composition contains titanium dioxide as a polishing agent to aid the cleaning and whitening of the surface of the teeth. As the effervescent composition is swept around the surface of the teeth and between the teeth, the titanium particles exert a mild abrasive action on the plaque adhering to the surface of the teeth.

EXAMPLE 15

The following effervescent dentifrice composition is prepared with the following ingredients in the amounts specified. All ingredients pass through a 320 mesh screen. The components are added together and thoroughly mixed to form a homogenous powder.

| Component | Amount |
| --- | --- |
| potassium bicarbonate | 15.20 grams |
| tartaric acid | 3.90 grams |
| J. M. Huber Corporation brand ZEO-49 silica | 4.20 grams |
| powdered wintergreen | 0.25 grams |
| NUTRASWEET brand artificial sweetener | 0.72 grams |
| sodium dodecyl sulfate | 0.13 grams |
| TOTAL | 24.53 grams |

EXAMPLE 16

The following effervescent dentifrice composition is prepared with the following ingredients supplied in powdered form. All ingredients pass through a 320 mesh screen. Components are added together and thoroughly mixed to form a homogenous powder. After thorough mixing, the powdered composition is stored in sealed containers.

| Component | Amount |
| --- | --- |
| sodium bicarbonate | 10.42 grams |
| citric acid | 0.25 grams |
| J. M. Huber Corporation brand ZEO-49 silica | 3.53 grams |

| Component | Amount |
| --- | --- |
| NUTRASWEET brand artificial sweetener | 0.61 grams |
| powdered wintergreen | 0.26 grams |
| menthol | 0.11 grams |
| sodium dodecyl sulfate | 0.08 grams |
| TOTAL | 17.24 grams |

The above composition was utilized in the same manner as the composition of Example 1. Optionally, the above composition can be further compounded with 1.0 grams of sorbitol and 0.25 grams of zinc stearate formed into tablets, each tablet weighing 750 milligrams. The tablets are sealed in bottles or in impervious metal foil packages to prevent absorption of water and reaction between the bicarbonate and acid.

EXAMPLE 17

An effervescent composition suitable for delivery in non-aqueous liquid vehicle is prepared from the following ingredients in the amounts indicated. All the ingredients are obtained in a fine powdered form, and all pass through a 320 mesh screen. The dry solid ingredients are mixed together to form a homogenous mass. The powder is then dispersed in the non-aqueous liquid vehicle to obtain a non-aqueous liquid mixture. The mixture is thoroughly shaken before a dosage is taken into the oral cavity to insure the proper dosage unit.

| Component | Amount |
| --- | --- |
| sodium bicarbonate | 15.00 grams |
| J. M. Huber Corporation brand ZEO 49 silica | 4.10 grams |
| ascorbic acid | 1.00 grams |
| citric acid | 2.00 grams |
| menthol | 0.15 grams |
| sodium perborate | 0.72 grams |
| NUTRASWEET brand artificial sweetener | 0.90 grams |
| powdered wintergreen | 0.40 grams |
| sodium dodecyl sulfate | 0.18 grams |
| glycerine | 4 fld. oz. |
| propylene glycol | 20 fld. oz. |
| ethyl alcohol (100%) | 1 fld. oz. |

The above formulation provides a liquid mixture that will give a dosage of about 1000 milligrams of the effervescent composition per fluid ounce of the liquid mixture.

EXAMPLE 18

Another example of an effervescent composition or plaque adsorbent oral composition is set forth in tabular form below. As with the other examples set forth above, the sodium bicarbonate, citric acid and precipitated silica are the active components providing effective plaque adsorption according to the present invention. The remaining components are present, for example, as flavoring agents or as excipients (tableting aids).

| Component | Amount % by wgt. |
| --- | --- |
| sodium bicarbonate | 47.20 |
| citric acid | 9.10 |
| microcellulose (#102, FMC) | 14.70 |

-continued

| Component | Amount % by wgt. |
|---|---|
| sodium lauryl sulfate | 0.70 |
| aspartame (NUTRASWEET brand) | 7.00 |
| predcipitated silica (J. M. Huber Corporation brand ZEO-49 silica) | 5.80 |
| peppermint flavor | 0.60 |
| menthol | 0.02 |
| magnesium stearate | 0.60 |
| sylox 15 | 0.17 |
| dicalciumphosphate (granular) | 11.30 |
| dicalciumphosphate (dentifrice grade) | 2.70 |

The composition of Example 18 was found to be particularly suitable for production, using a standard rotary tablet press, of a tablet form of the product of the invention. Preferably, the tablets were formed with an individual weight in the range of about 0.75–1.25 grams, more preferably about 1.1 gram per tablet.

The present invention further contemplates the plaque adsorbent or effervescent dentifrice composition disclosed above as one component in a kit of four components contemplated for use in combination to achieve enhance or effective preventative and remedial oral hygiene, including control of gum disease, dissolution of plaque and prevention of plaque accumulation in the oral cavity. The four components of the kit include (1) a debriding product, preferably a solution comprised chiefly of a flavored aqueous solution of sodium bicarbonate (5–10% by weight), (2) the plaque adsorbent or effervescent dentifrice tablet of the preceding disclosure and examples, (3) a product, preferably in the form of a viscous dilute aqueous solution or jelly, of hydrogen peroxide (1.5–6% by weight) or an equivalent hydrogen peroxide precursor, and (4) a bicarbonate dentifrice containing about 10–65% by weight of sodium or potassium bicarbonate salt or other equivalent bicarbonate salt.

As indicated above, the second component of the kit is discussed above with variations disclosed in Examples 1–18. The other three components of the kit are further defined below in Examples 19–21 followed by a description of the method of combined use of the four components for synergistically enhancing preventative and remedial oral hygiene.

EXAMPLE 19

A debriding product, preferably in the form of a flavored aqueous solution contains sodium bicarbonate as an essential active agent. Additional examples generally equivalent to Example 19 are also possible with the amount of sodium bicarbonate being varied throughout the range of about 5–10% by weight of the solution.

| Component | Amount % by wgt. |
|---|---|
| sodium bicarbonate | 8.00 |
| water | 91.00 |
| sodium benzoate | 0.50 |
| nonionic surfactant, e.g. polysorbate 20 (TWEEN 20) | 0.30 |
| menthol crystals | 0.20 |

The debriding solution is formed by placing the sodium bicarbonate and other components into solution in the water.

EXAMPLE 20

The third component of the kit, referred to above as a hydrogen peroxide solution or jelly is formed preferably as an aqueous solution or jelly with hydrogen peroxide as an essential ingredient. However, the product of Example 19 may be varied by adjusting the amount of hydrogen peroxide across the range of 1.5–6% by weight or by replacing the hydrogen peroxide with an equivalent hydrogen peroxide precursor.

| Component | Amount % by wgt. |
|---|---|
| water | 89.20 |
| hydrogen peroxide (35% by wgt. in water) | 8.60 |
| anionic surfactant, polyacrylic acid (Carbopol 934 from B. F. Goodrich) | 1.40 |
| triethanolamine (99% solution in water) | 0.75 |

In Example 20, the anionic surfactant and triethanolamine interact with the triethanolamine serving as a neutralizing agent relative to the surfactant for producing the preferred jelly composition.

EXAMPLE 21

The fourth component of the kit is a bicarbonate dentifrice preferably formed with sodium or potassium bicarbonate salt as an essential ingredient in the range of about 10–65% by weight of the dentifrice.

| Component | Amount % by wgt. |
|---|---|
| water | 14.04 |
| sodium saccharin | 0.10 |
| sodium benzoate | 1.00 |
| glycerin | 25.00 |
| carboxymethyl cellulose, 7mf | 1.00 |
| sorbitol (70% solution in water) | 8.00 |
| sodium bicarbonate | 40.00 |
| calcium carbonate | 10.00 |
| sodium hydroxide | 0.10 |
| wintergreen | 0.30 |
| menthol | 0.20 |
| titanium dioxide | 0.10 |
| sodium lauryl sulfate | 0.25 |

The bicarbonate dentifrice product can be made in a variety of compositions, for example by varying the amount of sodium bicarbonate across the range of about 10–65% by weight thereof or by employing another suitable bicarbonate salt such as potassium bicarbonate across the same range.

Particularly with relation to the third and fourth components of the kit, Examples 20 and 21 above, it is noted that U.S. Pat. No. 4,528,180 issued Jul. 9, 1985 to Schaeffer ostensibly disclosed compositions which were generally similar to the third and fourth components of the kit which were not contemplated for the combined method of use specified herein.

The present invention further contemplates a method of combined use for the four kit components as set forth above wherein the four components function synergistically for enhanced preventative and remedial oral hygiene, including control of gum disease, dissolution of plaque and prevention of plaque accumulation in the oral cavity.

The method of the invention contemplated for the kit includes use of the debriding solution prior to normal tooth brushing and/or before use of the third and fourth components, namely the hydrogen peroxide jelly and the bicarbonate dentifrice. The debriding solution is aliquoted (about 1 ounce) and placed in the oral cavity where it is swished around the teeth and gums, preferably for about 30 seconds to 2 minutes, then expulsed from the oral cavity.

The plaque adsorbent oral composition or effervescent dentifrice tablets are used from about 1–10 times daily, preferably about 3–5 times daily, and more preferably after meals and snacks and whenever a freshening of the oral cavity is desired. The tablets are chewed with the resulting salivary solution being swished and swirled, in a manner similar to use of the first components or debriding solution, around the teeth and gums for about 30 seconds up to about 10 minutes, preferably about 2–6 minutes, then expulsed from the oral cavity (or swallowed).

The third and fourth components, namely the hydrogen peroxide jelly and the bicarbonate dentifrice, are used in combination. The two products are directly applied to a toothbrush or similar applicator, from separate containers, to form a jelly-paste which is slightly effervescent. The effervescent combined product is then applied to the teeth and gums, preferably with a brushing technique similar to that commonly employed with a standard toothpaste or dentifrice in the daily practice of good orally hygiene. The application or brushing with the combined jelly-paste of the third and fourth components is continued preferably for about 1–5 minutes, then expulsed. Preferably, the oral cavity is rinsed with water following this step.

Accordingly, there has been described above a variety of examples of a plaque adsorbent oral composition or effervescent dentifrice product, preferably in the form of tablets. In addition, there has been described a combination or kit of four components including the plaque adsorbent oral composition or effervescent dentifrice tablet, together with three additional components including a debriding product or solution, a source of hydrogen peroxide, preferably a solution of hydrogen peroxide, and a bicarbonate dentifrice. Variations and modifications of the plaque adsorbent oral composition as well as the four component kit and method of combined use for the four components of the kit are contemplated in addition to the variations specifically set forth above. Accordingly, the scope of the present invention is defined only the following appended claims which are further exemplary of the invention.

What is claimed is:

1. An effervescent powder for oral use comprising:
    a) a non-aqueous, water soluble pharmaceutically acceptable carbon dioxide source selected from the group consisting of bicarbonate salt, carbonate salt, and mixtures thereof;
    b) a non-aqueous, water soluble, pharmaceutically acceptable acid source selected from the group consisting of organic acid, partial salt thereof, and mixtures thereof; and
    c) a precipitated amorphous silica.

2. A method for cleaning an oral cavity comprising the steps of:
    a) placing into an oral cavity an effervescent tablet or capsule of effervescent powder for oral use having a non-aqueous, water soluble, pharmaceutically acceptable carbon dioxide source selected from the group consisting of bicarbonate salt, carbonate salt, and mixtures thereof; a non-aqueous, water soluble, pharmaceutically acceptable acid source selected from the group consisting of organic acid, partial salt thereof; and
    (b) a precipitated amorphous silica.

3. A method of achieving enhanced preventative and remedial oral hygiene including for example control of gum disease, dissolution of plaque and prevention or minimization of plaque accumulation in the oral cavity, comprising the steps of
    (a) using a debriding product as a rinse in the oral cavity, the debriding product including sodium bicarbonate as an essential component in an effective amount,
    (b) dispersing a plaque adsorbent oral composition or effervescent dentifrice product as defined in claim 1 throughout the oral cavity at least once daily,
    (c) using a hydrogen peroxide product and bicarbonate dentifrice in combination and applying them to the teeth and gums with a brushing or massaging action at least once daily, the hydrogen peroxide product containing about 1.5–6% by weight of hydrogen peroxide or an equivalent hydrogen peroxide precursor and the bicarbonate dentifrice comprising about 10–65% by weight of a bicarbonate salt,
    steps (a)–(c) being carried out in combination at least one or more times daily in order to synergistically achieve enhanced preventative and remedial oral hygiene.

4. A combination of compositions in kit form for combined use to synergistically achieve enhanced preventative and remedial oral hygiene including control of gum disease, dissolution of plaque and prevention of plaque accumulation in the oral cavity, comprising
    (1) a debriding product containing an effective amount of sodium bicarbonate,
    (2) a plaque adsorbent oral composition or effervescent dentifrice as defined in claim 1,
    (3) a product containing an effective amount of hydrogen peroxide or an equivalent hydrogen peroxide precursor, and
    (4) a bicarbonate dentifrice containing an effective amount of a bicarbonate salt,
    the components of (1)–(4) being adapted for daily use in the oral cavity to synergistically achieve enhanced preventative and remedial oral hygiene.

* * * * *